United States Patent [19]

Groves

[11] Patent Number: 4,760,328
[45] Date of Patent: Jul. 26, 1988

[54] PARTICLE COUNTER HAVING ELECTRODES AND CIRCUITRY MOUNTED ON THE PANE OF THE ORIFICE

[75] Inventor: Michael R. Groves, Flemington, N.J.

[73] Assignee: Integrated Ionics, Inc., Dayton, N.J.

[21] Appl. No.: 859,294

[22] Filed: May 5, 1986

[51] Int. Cl.$^4$ ............................................. G01N 27/00
[52] U.S. Cl. ................................. 324/71.4; 324/71.1
[58] Field of Search .................... 324/71.1, 71.4, 446, 324/158 P; 377/11, 12

[56] References Cited

U.S. PATENT DOCUMENTS

| | | | |
|---|---|---|---|
| 3,238,452 | 3/1966 | Schmitt et al. | 324/71.4 X |
| 3,771,058 | 11/1973 | Hogg | 324/71.1 |
| 4,389,610 | 6/1983 | Schiebel et al. | 324/446 X |

Primary Examiner—Reinhard J. Eisenzopf
Assistant Examiner—Jack B. Harvey
Attorney, Agent, or Firm—Pennie & Edmonds

[57] ABSTRACT

An improved electronic particle counter is described in which the electrodes and at least part of the signal processing circuitry are integrally formed on the pane in which the orifice is located. The pane is formed from a wafer of sapphire of the grade customarily used in the manufacture of silicon-on-sapphire integrated circuits. A silicon layer is first formed epitaxially on one side of the wafer and integrated circuits are then formed in the silicon layer using conventional photolithographic techniques. Illustratively, the integrated circuits provide the same particle counting and particle sizing functions that are available in separate packages with state-of-the-art particle counters. An electrode is formed on the same side of the wafer as the integrated circuit by converting some of the epitaxial silicon to a conductive polysilicon or by depositing a metallic layer; and the electrode is connected to the signal input lead of the integrated circuit. A second electrode is then formed on the opposite surface of the wafer by deposition of a metallic layer. An orifice is formed in each pane in the sapphire by etching or drilling. Finally the wafer is diced so as to separate the individual panes.

9 Claims, 4 Drawing Sheets

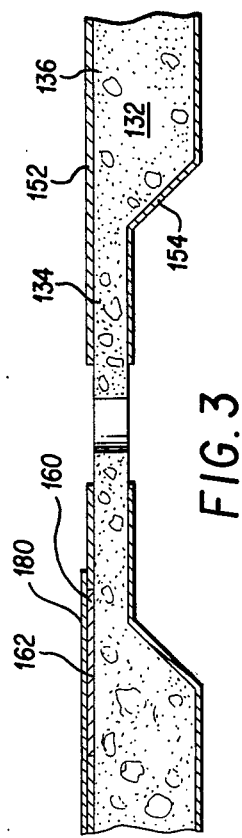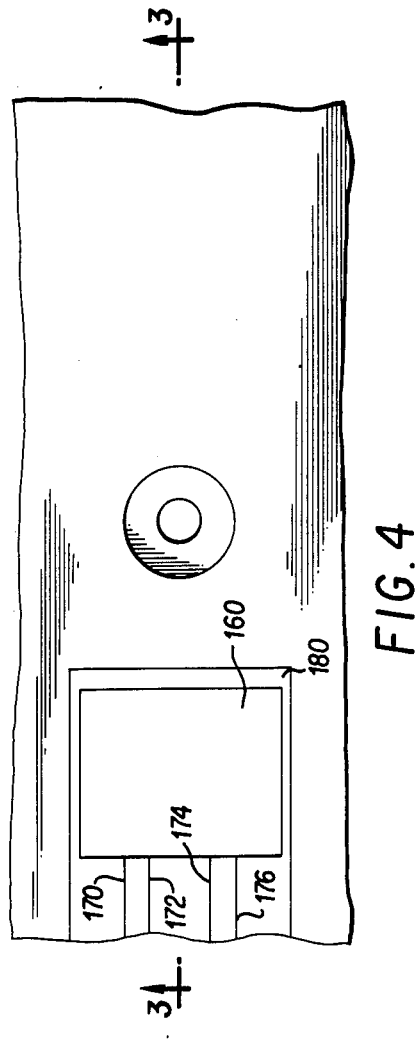

PARTICLE COUNTER HAVING ELECTRODES AND CIRCUITRY MOUNTED ON THE PANE OF THE ORIFICE

CROSS-REFERENCE TO RELATED PATENTS

Related patents are U.S. Pat. Nos. 2,656,508, 3,502,973, 3,502,974, 3,710,933 and 4,298,836 which are incorporated herein by reference.

BACKGROUND OF THE INVENTION

This relates to an improved particle counter of the Coulter (R) Counter type and to a method for its manufacture.

U.S. Pat. No. 2,656,508 describes a device for the electronic counting, sizing and analysis of microscopic particles in a fluid suspension. In that device, the fluid suspension is forced to flow through an orifice from one insulated vessel to another. A D.C. electric current is established between the two vessels by mounting electrodes in the two vessels. Since the only electrical path between the two vessels is through the fluid that flows through the orifice, an electric current flow and field are established in the orifice. The orifice and the resultant electric field in and around it constitute a sensing zone. As each particle passes through the sensing zone, the impedance of the contents of the sensing zone will change for the duration of the passage, thereby modulating the current flow and electric field in the sensing zone. The change in current flow and electric field produces a signal that is applied to a detector suitably arranged to respond to such change.

It has been proved that the change in impedance of the contents of the sensing zone as a particle passes through it is approximately proportional to the volume of the particle where the diameter of the orifice is smaller than the axial length of the orifice.

The impedance sensing principle has been extended to provide information concerning particle characteristics such as the composition and nature of the material constituting the particles, as disclosed in U.S. Pat. No. 3,502,974 to Coulter et al. and U.S. Pat. No. 3,502,973 to Coulter et al. These devices generally have at least two current sources, both of which are applied to the sensing zone simultaneously, one having a radio frequency and the other being a "zero frequency" direct current or, alternatively, having a sufficiently low frequency that the reactive part of the particle impedance has a negligible effect on the response of the apparatus. One of the useful particle descriptors that can be obtained from this dual source arrangement is known in the art as the "opacity" of the particles. In a general sense, opacity measures the difference in size as measured at radio frequency as compared to size measured at low or zero frequency.

As is appreciated in the art of cytology, any new particle descriptor that can be measured is useful in identifying, analyzing and sorting particles. For example, cells have a membrane of very high resistivity which is in the range of a dielectric. However, the internal portion of the cell is fairly conductive, with different types of particles having varying internal resisitivities. Also, it is contemplated that the pathological state of the cell will affect its internal resisitivity. Consequently, it is desirable to measure this internal resisitivity on a cell by cell basis. U.S. Pat. No. 4,298,836, for example, describes apparatus for measuring resisitivity. U.S. Pat. No. 3,710,933 describes an impedance sensing orifice that is used in combination with measurements of light absorbance, scattered light and fluorescent light.

As shown in FIG. 1, illustrative prior art particle counters comprise an inlet chamber 10, an outlet chamber 20, an orifice 30 interconnecting the chambers, viewing optics 40 and electronics 50. A liquid stream of individually suspended particles, originally from a pressurized reservoir (not shown), proceeds through a capillary tube 12 into chamber 10. A laminar liquid sheath, originally from another pressure reservoir (not shown), proceeds through tubes 14 so as to surround the stream of particles. As the liquid stream of particles exits from tube 12, hydrodynamic pressures reduce the diameter of the stream of particles as the stream obtains the velocity of the liquid sheath. The liquid sheath also acts to center the stream of particles so that particles pass through the orifice 30 along a center axis 18, with the elongated particles, if any, having their elongated axis aligned with the center axis 18. After leaving the orifice 30, the particles enter chamber 20. Chamber 20 has an inlet 22 and an outlet 24 for a suitable fluid which removes the suspended particles.

Orifice 30 is a microscopic hole that typically is machined in a pane 32 of jewelry-quality sapphire. The dimensions of the orifice are small enough that a single particle can be counted. To this end the orifice ordinarily has a diameter on the order of four-thousandth of an inch (100 micrometers) or less.

Electronics 50 comprises electrodes 52 and 54 in chambers 10, 20 respectively, a constant current supply 56 and signal processing elements 60. Electrodes 52 and 54 and constant current supply 56 are used to establish an electric current in chambers 10 and 20 which passes through orifice 30 and varies with the passage of particles through the orifice. The signal processing elements illustratively comprise an amplifier 62, a baseline restorer 64, trigger circuitry 66, counter 68, a peak detector 72, and size determining circuitry 74. Details of signal processing circuitry are well known in the art being disclosed, for example, in the above-referenced patents. The signal processing circuitry typically is mounted on a circuit board in a separate package apart from the inlet and outlet chambers.

SUMMARY OF THE INVENTION

I have devised an improved particle counter in which the electrodes and at least part of the signal processing circuitry are integrally formed on the pane in which the orifice is located.

In accordance with the invention, the pane that is used is formed from a wafer of sapphire of the grade customarily used in the manufacture of silicon-on-sapphire integrated circuits. As in the case of the fabrication of such circuits, several panes are simultaneously formed on a wafer using photolithographic techniques.

A silicon layer is first formed epitaxially on one side of the sapphire wafer and integrated circuits are then formed in the silicon layer using conventional photolithographic techniques. Illustratively, the integrated circuits provide the same particle counting and particle sizing functions that are available in separate packages with state-of-the-art particle counters.

Leads are then formed to provide power and ground to each integrated circuit as well as a signal input and a signal output. An electrode is formed on the same side of the wafer as the integrated circuit by converting some of the epitaxial silicon to a conductive polysilicon or by depositing a metallic layer; and the electrode is connected to the signal input lead of the integrated circuit. Advantageously, a guard layer of a grounded conductor is then formed on top of the integrated circuit and signal leads but insulated therefrom so as to minimize signal noise and to protect these elements from their environment. A second electrode is then formed on the opposite surface of the wafer by deposition of a metallic layer. An orifice is then formed in the wafer for each device that is to be made. Finally the wafer is diced so as to separate the individual panes or die.

Advantageously, the invention is practiced using semiconductor-grade sapphire wafers three or four inches (38 to 51 millimeters (mm.)) in diameter and 125–250 micrometers in thickness. The diameter of the orifice is about 50 micrometers and the thickness of the wafer in the region immediately surrounding the orifice is reduced to about 50 micrometers. The size of each device including the orifice, electrodes and integrated circuit after separation from the wafer is approximately 4 mm.×4 mm.

BRIEF DESCRIPTION OF DRAWINGS

These and other objects, features and advantages of the invention will be more readily apparent from the following detailed description of a preferred embodiment of the invention in which:

FIG. 3 is an enlargement of a portion of FIG. 2;

FIG. 4 is a top view of the same portion of FIG. 2; and

DETAILED DESCRIPTION OF PREFERRED EMBODIMENT

Figure 1:
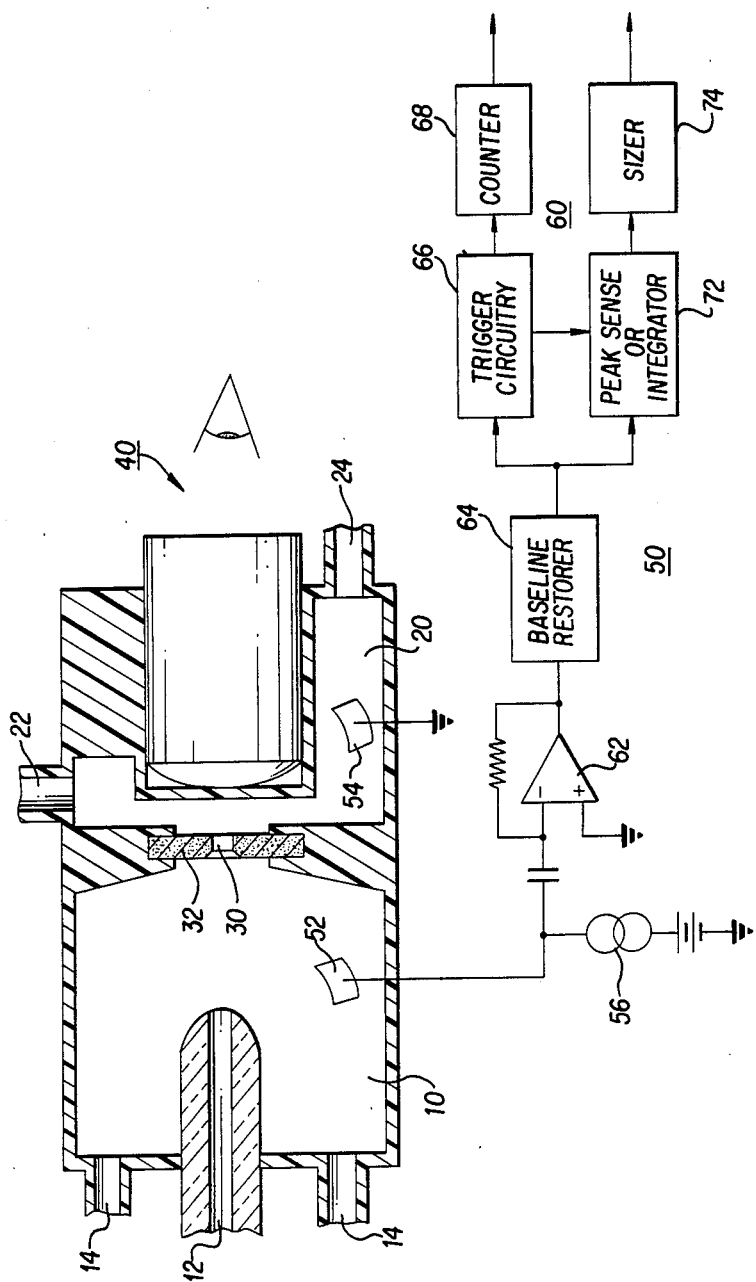
FIG. 1 is a schematic illustration of a prior art particle counter.
Figure 2:
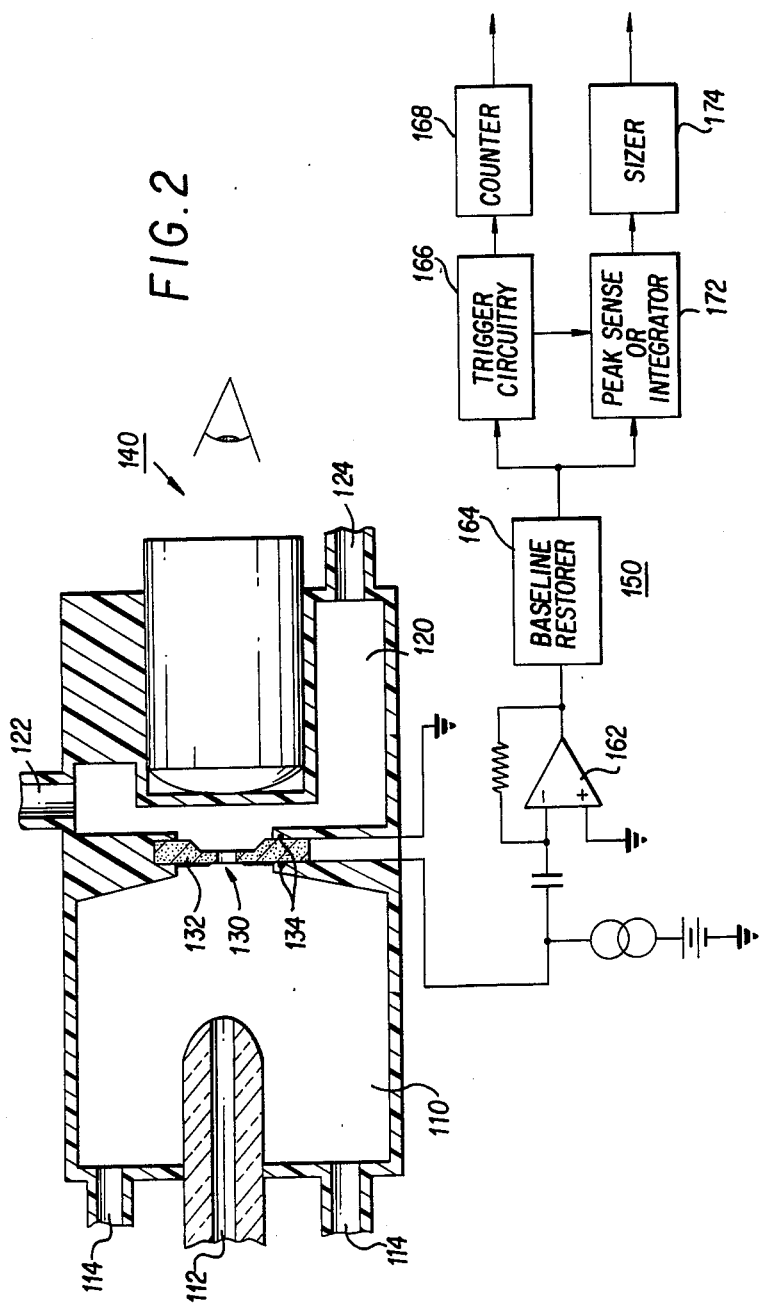
FIG. 2 is a schematic illustration of a preferred embodiment of the invention.
Figure 5:
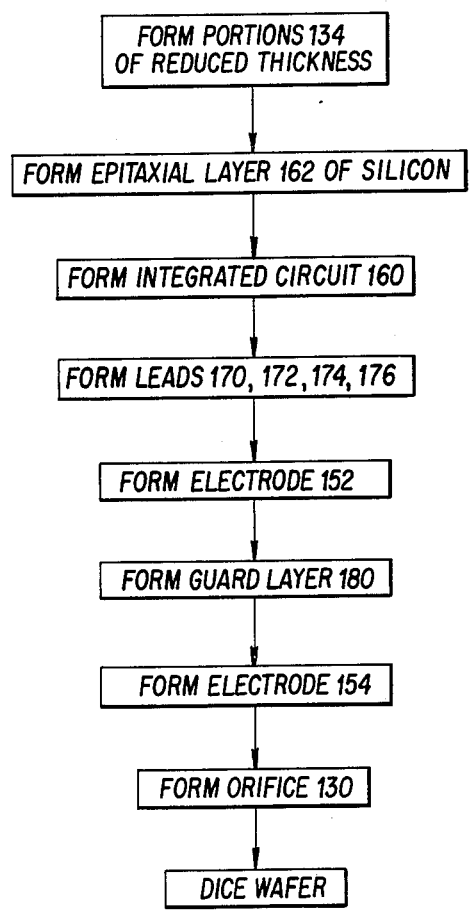
FIG. 5 sets forth several process steps used in the practice of the invention.

As shown in FIG. 2, a preferred embodiment of a particle counter of the present invention comprises an inlet chamber 110, an outlet chamber 120, an orifice 130, and viewing optics 140. Chambers 110 and 120 are electrically insulated from each other, but are interconnected by orifice 130. Each of these elements is similar to the corresponding element of FIG. 1 and bears the same number incremented by 100. As will become apparent, however, orifice 130 is formed in a wafer 132 that is considerably different from wafer 32 of FIG. 1.

As in the case of the apparatus of FIG. 1, a liquid stream of individually suspended particles, originally from a pressurized reservoir (not shown), flows through a capillary tube 112 into chamber 110. A laminar liquid sheath, originally from another pressure reservoir (not shown), flows through tubes 114 so as to surround the stream of particles. As the liquid stream of particles leaves capillary tube 112, hydrodynamic pressures reduce the diameter of the stream of particles as the stream obtains the velocity of the liquid sheath. The liquid sheath also acts to center the stream of particles so that particles pass through the orifice 130 along a center axis 118, with the elongated particles, if any, having their elongated axis aligned with the center axis 118. After leaving the orifice 130, the particles enter chamber 120. Chamber 120 has an inlet 122 and an outlet 124 for a suitable fluid which removes the suspended particles.

Orifice 130 is a microscopic hole in a pane 132 that is cut from a wafer of sapphire of the grade ordinarily used in the manufacture of silicon-on-sapphire integrated circuits. For details on the silicon-on-sapphire process, see S.M. Sze, *VLSI Technology*, p. 82 (McGraw-Hill 1983). The dimensions of the orifice are small enough that a single particle can be counted. Illustratively the orifice has a diameter of about 50 micrometers.

As shown more clearly in FIG. 3, pane 132 of sapphire has a thin portion 134 surrounding orifice 130 and a thicker portion 136 surrounding the thin portion. Portion 134 is thin enough that the thickness of the pane in that region is comparable to the diameter of the orifice, e.g., 50 micrometers. Portion 136 is the thickness of commercially available sapphire wafers used for integrated circuits. Such wafers are available in thicknesses of 125 and 250 micrometers and diameters of three or four inches (38 mm. or 51 mm.) or even larger. Typically, the size of each pane 132 is about 4 mm.×4 mm.

As is also shown in FIG. 3 and the top view of FIG. 4, electrodes 152, 154 are formed on the major surfaces of pane 132. These electrodes function in the same capacity as electrodes 52, 54 in the inlet and outlet chambers, respectively, of prior art particle counters but the electrodes are formed on the pane in which the chamber-connecting orifice 130 is located. In addition, at least some of the signal processing circuitry is formed as an integrated circuit 160 in an epitaxial silicon layer 162 formed on one major surface of pane 132. Advantageously, integrated circuit 160 and input and output signal lines 170, 172 are covered by a conductive guard layer 180 that is insulated from the integrated circuit and signal lines and which provides protection from the environment in which the pane is immersed as well as protection from spurious signals. The signal lines on the integrated circuit illustratively are connected to external signal leads by edge connectors (not shown) mounted on the edge of pane 132. A suitable seal 135 provides a fluid-tight interface between pane 132 and the exterior of the particle counter.

In accordance with the invention, numerous panes 132 are advantageously formed simultaneously in a wafer of commercially available sapphire of the grade used in the manufacture of silicon-on-sapphire integrated circuits. To form integrated circuits in the wafer of sapphire, a series of photolithographic masks are first designed that define the necessary features of the elements of the integrated circuits, signal lines, electrodes and the like.

To modify the thickness of the sapphire wafer in the region surrounding each orifice, the wafer is machined to a thickness of about 50 micrometers over a circular region of about 0.5 mm. diameter where each device is to be formed. Since each device measures about 4 mm.×4 mm. on the wafer, these regions of reduced thickness form a square array of spots on approximately 4 mm. centers. Advantageously, this operation is performed using standard step-and-repeat equipment. Alternatively, micro-machining techniques currently used to form 3-D microstructures in silicon can be used to thin the wafer. This is accomplished by photolithographic definition of the area to be thinned followed by dry or wet etching of the sapphire in that area.

The wafer is then processed in known fashion to form an epitaxial layer 162 of silicon on one side of the wafer. Typically, this layer is about one micrometer thick.

Next, integrated circuits 160 are formed by conventional techniques in the epitaxial silicon layer 162. The specific circuit that is formed is a matter of choice. Advantageously, it will include an amplifier which will provide significant improvement in signal to noise ratio. Other circuitry such as a baseline restorer, trigger circuitry and a particle counter may be provided so as to provide particle counting capability the same as provided by prior art circuits of FIG. 1. It may also include an integrator and size determining circuitry or any other signal processing circuitry useful in the analysis of particles as they flow through an orifice.

Connections are then formed between each integrated circuit 160 and its input signal line 170, output signal line 172, a power supply 174 and a ground 176. An electrode 152 is then formed for each device on the same side of the wafer as the silicon layer and it is connected to the input signal line 170 to the integrated circuit. The electrode may be made by converting portions of the silicon into conductive polysilicon or by depositing a metallic layer. In either case, the shape of the electrode is defined by conventional photolithographic techniques. Finally, a conductive layer 180 is deposited on top of the integrated circuit 160 and signal lines 170, 172 but insulated therefrom so as to guard the circuit and signal lines from electrical noise as well as protect it from the environment in which the wafer is immersed.

A second electrode 154 is then formed on the opposite major surface of each device by deposition of a metallic layer and the use of conventional photolithographic techniques to shape the electrode.

The orifice of each device is then formed in the wafer at each spot of reduced thickness. Advantageously, the orifice is formed by photolithographically defining the area where it is to be located and then etching the sapphire away using conventional etching technique. Alternatively, the orifice could be formed by drilling with a laser.

Upon completion of the electrodes, the wafer is then diced into individual panes. The panes are then tested and assembled into particle counters as shown in FIG. 2.

As will be evident to those skilled in the art, numerous variations may be made within the spirit and scope of the invention. While the invention has been described in the context of silicon-on-sapphire integrated circuit technology, it will be appreciated that other insulative substrates may be used in place of sapphire and that other semiconductor materials may be used in place of silicon. If desired hybrid circuits could also be used in place of some or all of the integrated circuitry. Numerous variations may also be practiced in shaping the electrodes that are formed on the surfaces of each pane of sapphire and in some applications it may be advantageous to locate an electrode in a portion of the device remote from the orifice and the pane in which it is formed.

If desired, multiple orifices of the same or different dimensions may be fabricated in accordance with the invention in the same pane of sapphire, and such orifices can be used in accordance with techniques known in the art.

What is claimed:

1. A particle counter comprising:
   an inlet chamber,
   an outlet chamber insulated from said inlet chamber,
   an orifice interconnecting the inlet and outlet chambers,
   an electrode in each of the two chambers for establishing an electric current between the two chambers through a fluid that flows through the orifice, and
   electronic circuitry for sensing changes in said current flow and/or an electronic field associated therewith,
   characterized in that
   said orifice is formed in a sheet of insulative material disposed between said first and second chambers,
   at least a portion of said electronic circuitry is mounted on said sheet of insulative material, and is sealed from said fluid, and is connected to external signal processing circuitry; and
   at least one of said electrodes is formed on a major surface of said sheet.

2. The apparatus of claim 1 wherein the insulative material is sapphire.

3. The apparatus of claim 2 wherein said electronic circuitry is formed in a semiconductor layer of silicon formed in said sheet of insulative material.

4. The apparatus of claim 1 wherein both electrodes are formed on opposing major surfaces of said sheet.

5. The apparatus of claim 1 wherein:
   a semiconductor layer is epitaxially formed on one surface of said sheet of insulative material, and
   at least a portion of said electronic circuitry is formed as an integrated circuit in said epitaxial semiconductor layer.

6. The apparatus of claim 1 wherein the portion of electronic circuitry mounted on said insulative layer includes an amplifier.

7. The apparatus of claim 1 wherein the electronic circuitry includes an amplifier, trigger circuitry and a counter for counting the number of particles that flow through said orifice.

8. The apparatus of claim 1 wherein the electronic circuitry can perform both R.F. and D.C. measurements.

9. The apparatus of claim 1 wherein a plurality or orifices are formed in the sheet of insulation material.

* * * * *